(12) United States Patent
Nougier et al.

(10) Patent No.: US 7,264,782 B2
(45) Date of Patent: Sep. 4, 2007

(54) REACTOR DEVICE HAVING AN ENCLOSURE MADE OF REFRACTORY MATERIAL AND A CONTAINMENT ENVELOPE FOR BRINGING ABOUT CHEMICAL REACTIONS REQUIRING HEAT EXCHANGE

(75) Inventors: Luc Nougier, Sainte Foy les Lyon (FR); Eric Lenglet, Rueil Malmaison (FR)

(73) Assignee: Institut Francais du Petrole, Malmaison Cedex (FR)

( * ) Notice: Subject to any disclaimer, the term of this patent is extended or adjusted under 35 U.S.C. 154(b) by 571 days.

(21) Appl. No.: 10/087,981

(22) Filed: Mar. 5, 2002

(65) Prior Publication Data
US 2002/0129930 A1    Sep. 19, 2002

(30) Foreign Application Priority Data
Mar. 5, 2001    (FR) ................................. 01 03191

(51) Int. Cl.
*B01J 19/00*    (2006.01)
(52) U.S. Cl. .................... 422/198; 422/199; 422/241
(58) Field of Classification Search ............. 422/198, 422/200, 204, 199, 240; 165/166
See application file for complete search history.

(56) References Cited

U.S. PATENT DOCUMENTS

| 4,612,982 A | * | 9/1986 | Grehier et al. ............. 165/166 |
| 5,270,016 A | * | 12/1993 | Alagy et al. ................ 422/199 |
| 5,554,347 A | | 9/1996 | Busson |
| 5,853,682 A | | 12/1998 | Busson |
| 6,027,635 A | | 2/2000 | Busson |

* cited by examiner

*Primary Examiner*—Glenn Caldarola
*Assistant Examiner*—Tom Duong
(74) *Attorney, Agent, or Firm*—Antonelli, Terry, Stout & Kraus, LLP.

(57) ABSTRACT

Reactor device (R) for carrying out chemical reactions requiring heat exchange, the reactor is elongate along an axis (XX'), and has, at a first end, at least one orifice (16) for supplying at least one reactant, at an opposite end, at least one orifice (18) for evacuating the effluents formed, a plurality of heat exchangers (12) separated by at least one internal partition (14) and passages for circulating the reactant or reactants and/or effluents, provided between the heat exchangers and the internal partitions. The reactor (R) has at least one enclosure (10) made of refractory material providing heat insulation and containing a heat exchangers (12) and internal partitions (14). The enclosure is contained in an envelope (20) to contain the reactant or reactants and/or effluents circulating inside the reactor.

16 Claims, 2 Drawing Sheets

REACTOR DEVICE HAVING AN ENCLOSURE MADE OF REFRACTORY MATERIAL AND A CONTAINMENT ENVELOPE FOR BRINGING ABOUT CHEMICAL REACTIONS REQUIRING HEAT EXCHANGE

The present invention relates to a reactor device for bringing about chemical reactions requiring heat exchange, particularly for bringing about endothermal reactions.

This device can be used in particular to bring about reactions such as steam cracking, hydrocarbon pyrolysis, catalytic dehydrogenation, steam reforming, or hydrogen sulfide ($H_2S$) thermal cracking reactions.

This device is particularly applicable to reactions taking place at a pressure less than, equal to, or greater than atmospheric pressure, often equal to or greater than this pressure, usually greater than atmospheric pressure, and normally at a high temperature, i.e. often higher than 150° C.

The reactor device is intended principally for handling reactions taking place at high temperatures such as those taking place at a temperature of at least 350° C. and in a potentially coking medium where the catalytic effects of metal walls must be avoided.

U.S. Pat. No. 5,554,347 teaches a particular form of a reactor with several rows of heating and/or heat extraction means.

According to the teaching of this document, the reactor used has heating means supplied by a mixture of combustible gas and gaseous oxidizer for generating the power required for the reaction, and walls of a special shape that not only increase heat transfers due to radiative wall-wall exchanges but also control the residence time of the gases in the reactor.

U.S. Pat. No. 5,321,191 teaches a reactor used to carry out a hydrocarbon thermal pyrolysis method comprising several rows of electrical heating means surrounded by sheaths disposed in layers that are essentially parallel to each other and perpendicular to the axis of the reactor in order to provide spaces or passages for circulation of the gaseous mixtures and/or effluents between the sheaths and/or between the sheaths and internal partitions separating two parallel sheath layers.

Implementation of these technologies has a number of advantages over ceramic technologies previously developed, for example that described in U.S. Pat. No. 4,780,196 that relates to hydrocarbon steam cracking in order to produce essentially light olefins, for example ethylene and/or propylene, and also that described in U.S. Pat. No. 4,973,777 relating to heat conversion of methane into hydrocarbons with higher molecular weights.

By comparison with the prior art teaching, substantial improvements can still be made in particular to facilitate the design and operating ease of the reactor, ensure its safety, and increase its reliability.

The present invention relates to a reactor device for carrying out chemical reactions requiring heat exchange, said reactor, which is elongate along one axis, having, at a first end, at least one means for supplying at least one reactant and, at an opposite end, at least one means for evacuating the effluents formed, and having a plurality of heat exchange means separated by at least one internal partition participating in controlling the residence time of the reactant or reactants and increasing the heat exchange surface inside the reactor, and passages for circulating the reactant or reactants and/or effluents, provided between said heat exchange means and said internal partitions, characterized in that the reactor has at least one enclosure made of a refractory material ensuring heat insulation and containing the heat exchange means and internal partitions, and in that said enclosure is contained in an envelope containing the reactant or reactants and/or effluents circulating inside said reactor.

The internal partitions may be made of modular elements.

The internal partitions may be made of abutting modular elements whose shape is designed for obtaining the desired residence time in the reactor for the reactant or reactants and the effluents.

The internal partitions may be formed of non-abutting modular elements whose shape is designed for obtaining the desired residence time in the reactor for the reactant or reactants and the effluents.

The cross section of the containment envelope is substantially quadrilateral.

The reactor may have an outer shell whose cross section is substantially circular and whose inside diameter is substantially equal to the largest dimension of the outside diagonal of the containment envelope.

The enclosure may be made of an inorganic refractory material and the containment envelope may be made of a metal.

The enclosure may have means for linking and/or anchoring to the containment envelope.

The enclosure may be made of a refractory material chosen from porous ceramics, nonporous ceramics, refractory concretes, and aluminous concretes.

The enclosure may be adjusted to the containment envelope in such a way as to prevent gas bypasses between the outside of said enclosure and the inside of said envelope.

The reactor may have means for assembling and disassembling the heat exchange means as well as internal partitions and at least one means for accessing the inside of the reactor.

The invention will be better understood from the description of several embodiments, provided on a purely illustrative but not limiting basis, with reference to FIGS. 1 to 4 attached to the present description:

Figure 1:
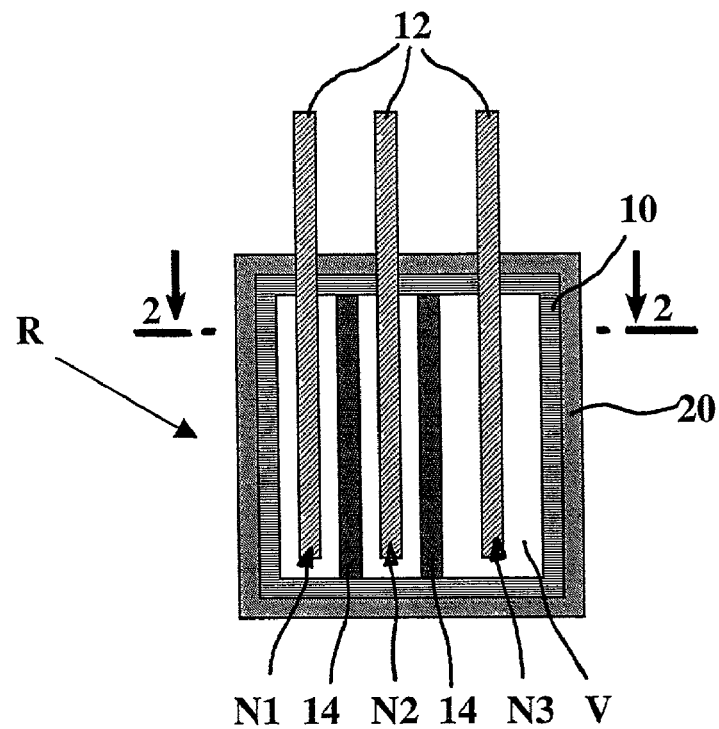
FIG. 1 is a cross section along line 1-1 in FIG. 2 of a reactor device according to the invention.
Figure 2:
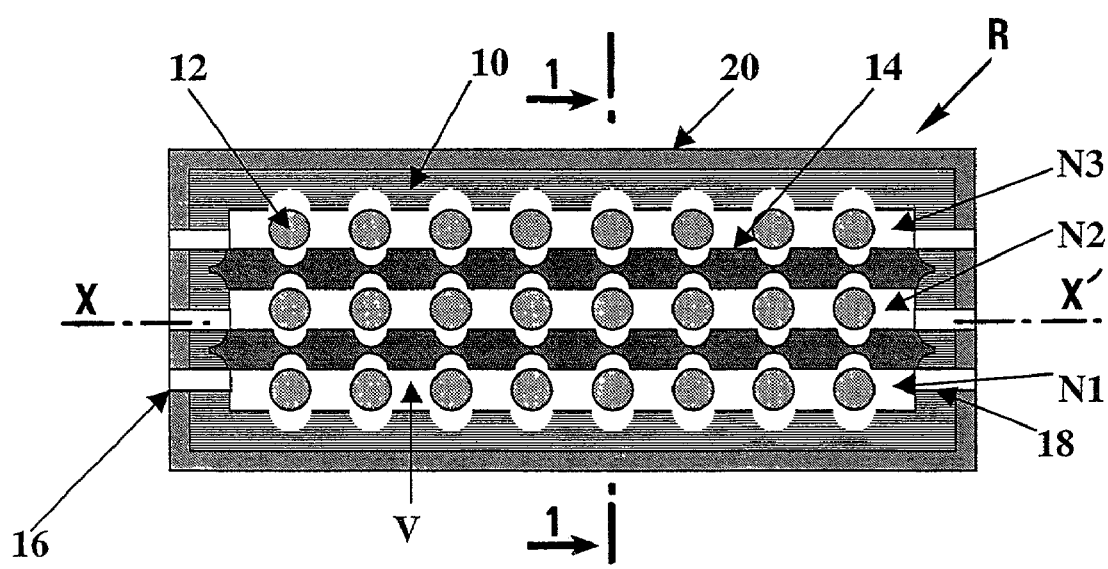
FIG. 2 is a schematic view in lengthwise section along line 2-2 in FIG. 1 of the reactor device.

As shown in FIGS. 1 and 2, reactor R, which is elongate in shape along a lengthwise axis XX', has an enclosure 10 delimiting a hollow internal volume V in which heat exchange means 12 in the form of sheaths and internal partitions 14 are disposed.

In these figures, enclosure 10 is square in cross section, but any other cross section may be considered such as a rectangle or circle.

The sheaths, which are made of nonporous industrial ceramics and contain a gas burner or an electrical resistor or a cooling tube, which in this case can also be made of metal, are disposed substantially perpendicularly to axis XX' and substantially parallel to each other in order to form rows or layers of sheaths N1, N2, N3 that are substantially parallel to each other.

Internal partitions 14 for controlling the residence time and/or generating an additional exchange surface are disposed between these layers and/or between these layers and the wall of enclosure 10.

In addition, the reactor has orifices 16 for introducing gaseous reactants and orifices 18 for exhausting the gaseous effluents containing the reaction products (FIG. 2).

A containment envelope 20, preferably made of metal, whose role is to provide impermeability to the process gases, is provided outside and around enclosure 10.

This envelope has a section that is preferably substantially identical to that of enclosure 10, in this case a square, and in the example shown, has inside dimensions substantially equal to the outside dimensions of enclosure 10.

Enclosure 10 has a wall that may be made of high-temperature refractory materials or a ceramic, the purpose of which is to provide heat insulation of the reactor in order to keep the wall of containment envelope 20 at an acceptable temperature.

Advantageously, to provide better resistance to the pressures prevailing in volume V of enclosure 10, the sharp corners of the square section of enclosure 10 and envelope 20 may be rounded.

Thus, enclosure 10 has a dual role: a heat insulator to protect the outer containment envelope of the reactor, and a shaper generating the internal space necessary for its participation in controlling the flow and residence time of the fluids circulating in the reactor.

One embodiment of this wall of enclosure 10 is based on coating technologies employing refractory concretes, such as in particular those used in the refining industry, for example in fluid catalytic cracking (FCC).

The concrete may be installed with anchoring techniques similar to those employed in FCC or in circulating fluidized beds (see: R. E. Woods and S. Patel, Second FCC Forum, May 15-17, 1996, The Woodlands, Texas or Fluidized Bed Combustion, Volume 2, ASME). V anchors, S bars, or hexmesh can be used. The V anchors that are commoner for refractory concretes several centimeters thick in low-erosion or non-erosion environments are preferred, however. The number of anchors will be determined on a case-by-case basis, bearing in mind that the new refractory concretes are highly stable and have very low expansion coefficients, so that the number of anchors can be considerably reduced.

Aluminous concretes such as Secar 70 or Super Secar 80, or materials based on zirconium, torine, or alumina are preferably used. This aluminous concrete can be single-layer or double-layer to improve its heat insulation. This layer can be porous but must fit the metal wall to prevent gas bypasses. These materials must be usable under high temperature conditions: up to 1500° C. for certain applications and preferably 1200° C. for hydrocarbon pyrolysis applications or even 1000° C. for steam cracking, for example.

This wall of enclosure 10 may have relative permeability (or, to use an equivalent term in the sense of the present description, non-zero porosity allowing gas to pass through its structure) provided it is preferably in direct contact with the metal wall of envelope 20 to prevent gas bypasses between the wall of metal envelope 20 and the refractory material of said wall of enclosure 10.

Various applications are possible for refractory concretes.

They are preferably applied by vibration pouring. With this technique, the refractory concrete is mixed with water according to the specifications of the manufacturer. The mixture thus obtained is poured between a wall previously fitted with the necessary anchors and a mold installed inside the reactor to define the thickness of the concrete layer and the specific shape of the inside wall. Vibrators installed on the wall facilitate concrete pouring, eliminating any air pockets and compacting the concrete. This technique is preferable because it enables relatively complex shapes to be created in the reactor inside wall.

A pneumatic system for spraying the refractory material against a wall to be coated may also be used in the context of the invention. A pre-mixture of concrete+water (5 to 15% by weight of water in general) is introduced into the gun. Additional water is then added through nozzles distributed on the neck of the spray gun to meet the specifications of the concrete manufacturer.

Depending on the geometric constraints of the method employed (residence time), the concrete may be sprayed, applied manually, or poured using vibration.

Of course, without departing from the framework of the invention, the wall carrying the anchoring means can be dispensed with and replaced by an additional mold that is removed together with the mold located inside the reactor once the operations are complete.

In any event, a concrete layer will be maintained that is relatively thin but thick enough to ensure heat insulation while maintaining the integrity of the latter.

Without this being limitative, the thickness is usually approximately 5 to approximately 100 centimeters, often approximately 10 to approximately 60 centimeters, and usually approximately 10 to 20 centimeters.

Anchors made of metal for example will be made to keep the concrete near the metal wall of envelope 20, for example at a relatively constant distance from the wall of enclosure 10 or directly in contact with this wall.

In any event, only the concrete layer is applied in a first step; the space available in the reactor allows this application and its control by an operator from within the reactor itself.

The wall of envelope 20 is usually approximately 0.5 to approximately 50 centimeters thick, often approximately 1 to approximately 20 centimeters thick, and usually approximately 2 to approximately 10 centimeters thick.

Once the concrete is in place, the internal partitions 14 are installed, for example through a near-total opening in one of the faces of the reactor or through a manhole.

These internal partitions are made in a single stack or from assembled bricks made of refractory materials. They are simply placed on the concrete floor of the reactor or set in position and pinned together or attached by the operator using any other equivalent means. They may be abutting or non-abutting.

The materials used for these internal partitions may be of the same type as the materials used for making the wall of enclosure 10 but it is preferable to choose materials with good heat conductivity such as silicon carbide (SiC), which makes the reactor thermally uniform and limits the risks of conversion profiles in the reactor.

These internal partitions 14 may be made of any known refractory material in the framework of the invention (for example refractory concretes, SiC, alumina, or mulite).

These internal partitions 14 are modular so that the operator can install or remove them and, in the latter case, can thus clear out all or part of volume V of the reactor, enabling the operator to enter the reactor to maintain it, particularly to maintain the wall of enclosure 10.

Heat exchange means 12 are usually installed by upper flanges once the wall of enclosure 10 and partitions 14 have been installed. These heat exchangers, installed vertically at the upper part of the reactor as shown in FIG. 1, may also be installed horizontally or vertically in the lower part of the reactor in another embodiment. One ingenious method is to install them alternately from one side to the other (head to foot) to increase heating density and hence reduce the residence time in certain applications (not shown in the figures).

For example, an indirectly cooled horizontal reactor with a total useful length of 25 meters and a square cross section 2.5 meters on the side, with a configuration similar to that shown schematically in FIG. 1, may be used.

Initially, the refractory concrete wall of enclosure 10 is applied to the wall of envelope 20 using the vibrational poured concrete method. This refractory concrete wall of enclosure 10 has semi-cylindrical recesses on the inner surface in which the heating or cooling elements will eventually be placed.

Once the wall of enclosure 10 is in place, the central stacks are laid to form internal partitions 14, which are placed on the floor of the reactor and are made of elementary silicon carbide bricks assembled together by the operator inside the reactor.

As can be seen in FIG. 2, each lengthwise face of partitions 14 also has semi-cylindrical recesses intended partially to contain heat exchange means 12.

The reactor is heated by burners known as radiant burners, having a silicon carbide heating sheath and a combustion head. The latter, having 180 heating elements disposed vertically, are introduced by upper flanges with no intervention from inside the reactor being necessary.

An annular space for circulation of the reactant gas is created between the burners and the reactor walls; the thickness of this annular space is 3 centimeters.

The last five meters of the reactor are equipped with cooling tubes for rapid cooling of the reactive gas before it leaves the reactor.

The feedstock, preheated to 750° C., is introduced through inlet orifices 16 and a heat profile is then imposed in the reactor by regulation comprising several zones regulated by thermocouples disposed in the spaces where the material circulates.

When it leaves the heating zone, this material is raised to a temperature of 930° C. to achieve a 90% conversion.

In the second part of the reactor (the last five meters), the material is cooled to approximately 600° C. by double-envelope tubes so that high-pressure steam can be obtained. The quencher classically used in steam cracking is introduced directly into the reactor in the present case.

The feedstock consists of ethane diluted with water vapor in a water-hydrocarbon mass ratio of 0.3. The total gas flow in the reactor is 87,000 t/year. Under reactor output conversion conditions, calculated using a model combining heat transfers and kinetics correlated to the results of a small pilot based on the same technology, it is 90%.

Figure 3:
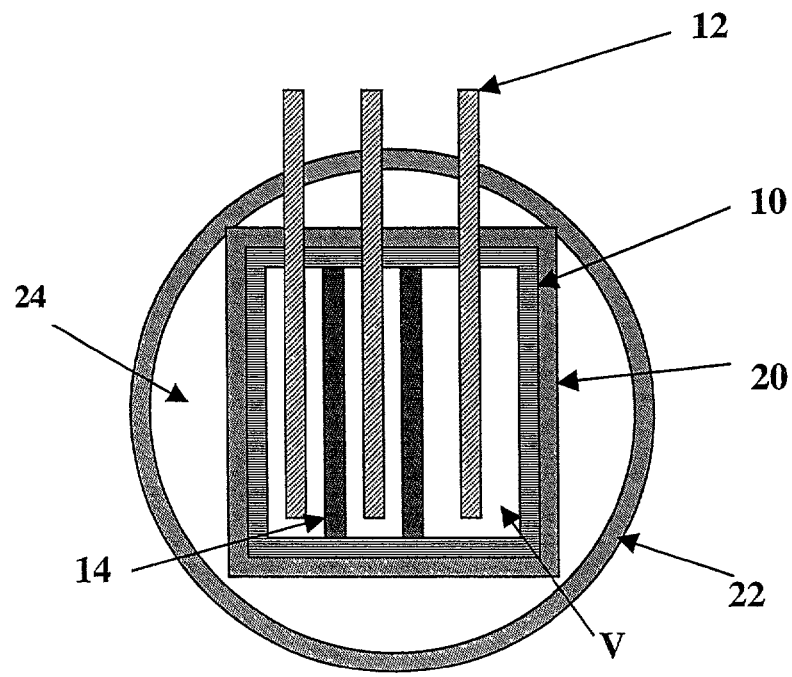
FIG. 3 is a cross section of a variant of the reactor device in FIG. 1.

Reference will now be made to FIG. 3, showing the particular case of a device according to the invention having an outer shell 22, preferably made of metal, which may be necessary for higher-pressure operation in the method of choice (greater than 2 bars absolute, for example).

This shell preferably has a circular cylindrical section whose diameter is essentially equal to the largest dimension of envelope 20 and delimits a free space 24 between said shell and said envelope.

Figure 4:
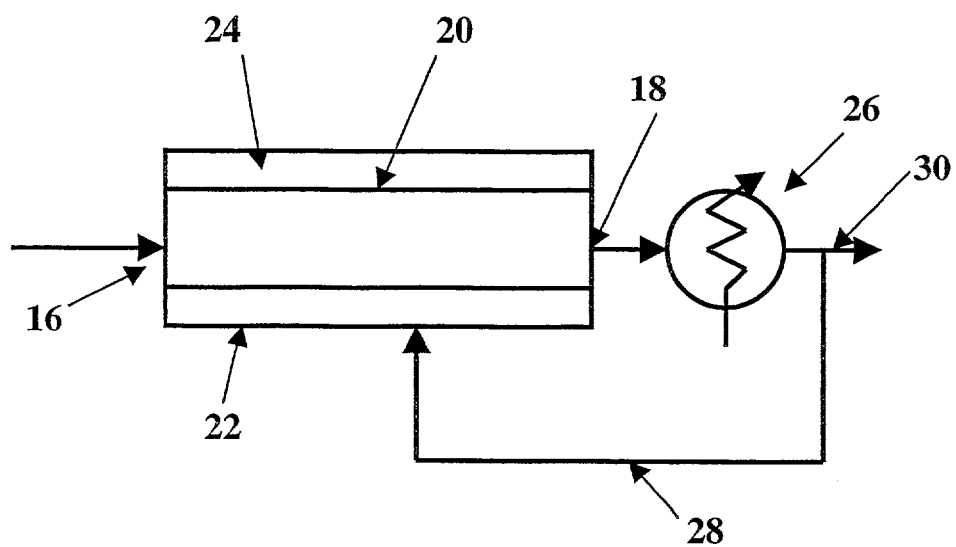
FIG. 4 is a diagram of a reactor device according to the invention.

FIG. 4 is a diagram of a device entering into the framework of the invention, comprising a heat exchanger 26 in which the hot gases leaving reactor R are cooled to an acceptable temperature by carbon steel elements, namely usually less than approximately 400° C., and shows a method of pressure balancing.

The space 24 generated by the wall of envelope 10 and that of outer shell 22 is connected by a line 28 directly either downstream in the case shown in FIG. 4 or upstream of the reactor for another application in a zone where the reactants are cooled for example by a heat exchanger 26 to an acceptable temperature by carbon steel, namely a maximum of 400° C. This line 28 is not designed to sweep zone 24 continuously but provides continuous pressure balancing if the wall of envelope 20 was not designed to withstand the process pressure and potential pressure variations in process line 30.

The present invention also relates to the use of the device according to the invention for bringing about thermal pyrolysis of hydrocarbon feedstocks included in the group of hydrocarbons principally containing ethane and hydrocarbons consisting principally of naphtha.

It also relates to the use of the device according to the invention for bringing about a dehydrogenation reaction of a hydrocarbon feedstock containing principally saturated hydrocarbons.

It also relates to the use of the device according to the invention for bringing about a dehydrogenation reaction of a hydrocarbon feedstock chosen from the group formed by hydrocarbon feedstocks containing principally propane and hydrocarbon feedstocks containing principally ethylbenzene.

It also relates to the use of the device according to the invention for bringing about a thermal cracking reaction of a feedstock containing hydrogen sulfide, usually containing principally $H_2S$.

As defined by the present invention, the term "principally containing" means that the feedstock contains at least 50 wt. % of the hydrocarbon compound mentioned or the hydrocarbon cut mentioned.

The invention claimed is:

1. Reactor device for carrying out chemical reactions requiring heat exchange, said reactor, which is elongate along an axis, having, at a first end, at least one means for supplying at least on reactant and, at an opposite end, at least one means for evacuating the effluents formed, and having a plurality of heat exchange means separated by at least one internal partition participating in controlling the residence time of the reactant or reactants and increasing the heat exchange surface inside the reactor, and passages for circulating the reactant or reactants and/or effluents, provided between said heat exchange means and said internal partitions, characterized in that the reactor has at least one enclosure made of a refractory material ensuring heat insulation and containing the heat exchange means and the internal partitions, in that said enclosure is contained in an envelope containing the reactant or reactants and/or effluents circulating inside said reactor, in that the enclosure is fitted to the containment envelope in such a way as to prevent gas bypasses between the outside of said enclosure and the inside of said envelope, and in that the containment envelope is provided within an outer shell whose cross section is substantially circular and whose inside diameter is substantially equal to the largest dimension of the outside diagonal of the containment envelope.

2. Device according to claim 1 in which the internal partitions are made of modular elements.

3. Device according to claim 2 in which the internal partitions are formed of abutting modular elements with a shape designed to obtain the desired residence time inside the reactor for the reactant or reactants and the effluents.

4. Device according to claim 2 in which the internal partitions are made of non-abutting modular elements with a shape designed to obtain the desired residence time inside the reactor for the reactant or reactants and the effluents.

5. Device according to claim 1 characterized in that the internal partitions have recesses for receiving the heat exchange means.

6. Device according to claim 1 in which the cross section of the containment envelope is substantially quadrilateral in shape.

7. Device according to claim 1 in which the enclosure is made of an inorganic refractory material and the containment envelope is made of a metal.

8. Device according to claim 1 in which the enclosure has linking and/or anchoring means to the containment envelope.

9. Device according to claim 1 in which the enclosure is made of a refractory material chosen from porous ceramics, nonporous ceramics, refractory concretes, and aluminous concretes.

10. Device according to claim 1 characterized by having means for assembling and disassembling the heat exchange means as well as the internal partitions and at least one means for accessing the inside of reactor.

11. Use of the device according to claim 1 to bring about thermal pyrolysis of a hydrocarbon feedstock included in the group of hydrocarbon feedstocks principally containing ethane and hydrocarbon feedstocks principally formed by naphtha.

12. Use of the device according to claim 1 for bringing about a dehydrogenation reaction of hydrocarbon feedstock principally containing saturated hydrocarbons.

13. Use of the device according to claim 1 to bring about a dehydrogenation reaction of a hydrocarbon feedstock chosen from the group formed by hydrocarbon feedstocks principally containing propane and by hydrocarbon feedstocks principally containing ethylbenzene.

14. Use of the device according to claim 1 to bring about a thermal cracking reaction of a feedstock principally containing hydrogen sulfide.

15. Device according to claim 1 wherein the outside of said enclosure is in direct contact with the inside of said envelope.

16. Device according to claim 1 wherein the outside of said enclosure has a section and dimension substantially equal to that of the inside of said envelope.

* * * * *